United States Patent

Rudko et al.

[11] Patent Number: 5,832,929
[45] Date of Patent: Nov. 10, 1998

[54] VIDEO ASSISTED THORACOSCOPIC TRANSMYOCARDIAL REVASCULARIZATION SURGICAL METHOD

[75] Inventors: Robert I. Rudko, Holliston; Stephen J. Linhares; Charles Christopher Negus, both of Taunton, all of Mass.

[73] Assignee: PLC Medical Systems, Inc., Franklin, Mass.

[21] Appl. No.: 620,270

[22] Filed: Mar. 22, 1996

[51] Int. Cl.⁶ ........................................ A61B 19/00
[52] U.S. Cl. ................... 128/898; 606/7; 606/15
[58] Field of Search ..................... 600/114, 117; 128/898; 606/15, 16, 7

[56] References Cited

U.S. PATENT DOCUMENTS

| | | | |
|---|---|---|---|
| 4,920,413 | 4/1990 | Nakamura et al. | 600/118 |
| 5,389,096 | 2/1995 | Aita et al. | 606/15 |
| 5,417,210 | 5/1995 | Funda et al. | 128/653.1 |
| 5,441,059 | 8/1995 | Dannan | 128/898 |
| 5,441,507 | 8/1995 | Wilk | 606/139 |
| 5,452,733 | 9/1995 | Sterman et al. | 128/898 |
| 5,554,152 | 9/1996 | Aita et al. | 606/7 |
| 5,571,215 | 11/1996 | Sterman et al. | 623/66 |
| 5,588,949 | 12/1996 | Taylor et al. | 600/166 |

*Primary Examiner*—Mickey Yu
*Assistant Examiner*—Kelly O'Hara
*Attorney, Agent, or Firm*—Iandiorio & Teska

[57] ABSTRACT

A video assisted thoracoscopic transmyocardial revascularization (TMR) surgical method includes making at least two spaced incision ports between the ribs of a patient proximate the patient's heart; inserting through one of the ports a thoracoscopic TMR handpiece assembly for creating a channel through the heart wall; inserting through the other incision port a thoracoscope connected to a video display system; viewing the heart of the patient through the video display system and positioning the handpiece assembly relative to the heart; and actuating the handpiece assembly to create a channel through the wall of the patient's heart.

7 Claims, 12 Drawing Sheets

VIDEO ASSISTED THORACOSCOPIC TRANSMYOCARDIAL REVASCULARIZATION SURGICAL METHOD

FIELD OF INVENTION

This invention relates to a video assisted thoracoscopic transmyocardial revascularization surgical method.

BACKGROUND OF INVENTION

Presently transmyocardial revascularization (TMR) is effected via a limited left thoracotomy. A longitudinal incision of four inches or more is made parallel to and between the fourth and fifth ribs and the ribs are spread apart approximately four inches so the surgeon can see the heart and reach in and apply the TMR handpiece to the wall of the beating heart. The left lung is normally deflated using a dual lumen endotracheal tube to make the heart more accessible. The heart is imaged using transesophogeal echo ultrasound. The patient is monitored by an EKG connected to a laser so that the laser can be fired only during a predetermined interval of the heartbeat after the surgeon calls for a firing. This creates a channel through the heart wall. The surgeon places his finger over the channel to stanch the blood flow until clotting occurs. The procedure is repeated until the desired number of channels are created, typically 20 to 30 but often as few as 5 or as many as 50. While this technique has achieved excellent results there are a number of shortcomings. There is considerable post-operative pain due to the spreading of the ribs which can lead to other problems: chest pain that hampers breathing can contribute to pneumonia. The large incision creates greater potential for infection and longer recovery time.

SUMMARY OF INVENTION

It is therefore an object of this invention to provide an improved video assisted thoracoscopic (VAT) transmyocardial revascularization (TMR) surgical method.

It is a further object to provide such a VAT TMR which produces less pain, less chance of infection and faster recovery.

The invention results from the realization that a truly improved VAT TMR surgical method can be achieved by making small incision ports between the ribs of a patient, inserting a thoracoscopic TMR handpiece and a thoracoscope through the ports and viewing through the thoracoscope the area of the heart to be operated on to position the handpiece and then actuating the handpiece to create a channel through the wall of the heart.

This invention features a video assisted thoracoscopic transmyocardial revascularization (TMR) surgical method including making at least two spaced incision ports between the ribs of a patient proximate the patient's heart, inserting through one of the ports a thoracoscopic TMR handpiece assembly for creating a channel through the heart wall, inserting through the other incision port a thoracoscope connected to a video display system, viewing the heart of the patient through the video display system and positioning the handpiece assembly relative to the heart, and actuating the handpiece assembly to create a channel through the wall of the patient's heart.

In a preferred embodiment the step of actuating the handpiece assembly may include sensing the contraction and expansion of the heart and actuating the handpiece assembly only at a predetermined time in the expansion and contraction of the beating heart. The handpiece assembly and thoracoscope positions may be interchanged and the actuation of the handpiece assembly may be repeated. The video display system may include a light source, a video camera and a monitor. The handpiece assembly may include an elongate barrel having a narrow width sized to fit between the ribs of a patient, an elongate handpiece extending from the barrel and having a similarly narrow width commensurate with the barrel, and a contacting surface on the distal end of the handpiece for contacting the wall of the patient's heart, the contacting surface having a width in a first dimension which is approximately that of the handpiece for fitting between the ribs of a patient and having a width in a second dimension which is larger to effect an area of the contacting surface which is substantially larger than the cross-sectional area of the handpiece.

The method may further include withdrawing the handpiece from its incision port and inserting through that incision port forceps with a sponge to cover the channel created through the heart wall and stanch blood flow. The method may include positioning the patient on his right side in the lateral decubitus position with the left rib cage exposed.

DISCLOSURE OF PREFERRED EMBODIMENT

Other objects, features and advantages will occur to those skilled in the art from the following description of a preferred embodiment and the accompanying drawings, in which.

Figure 1A:
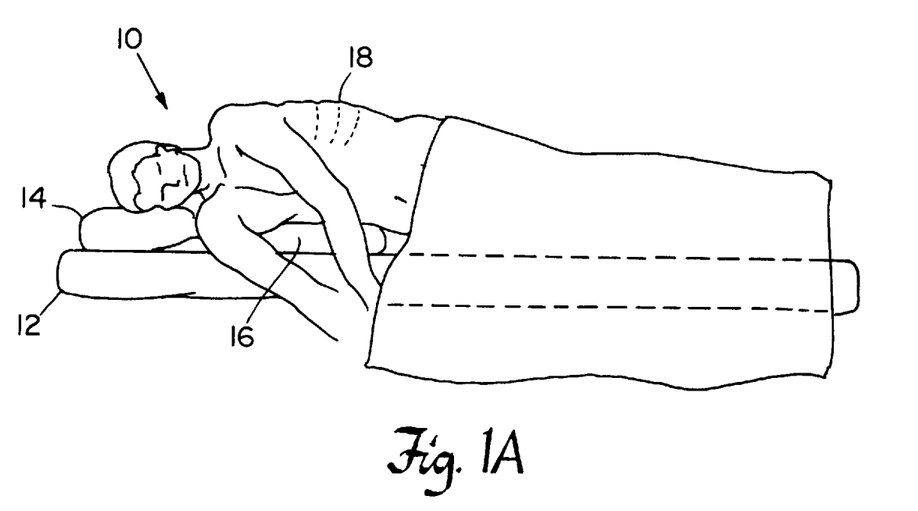
FIG. 1 is a schematic view of a patient positioned on his right side on an operating table with his left ribs flexed preparatory to execution of the surgical method according to this invention.
Figure 1B:
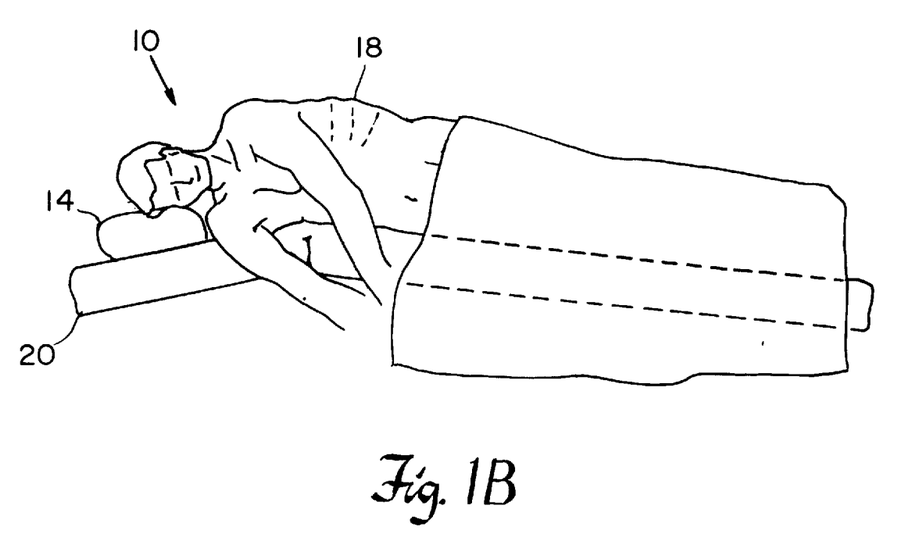
FIG. 1B is a view similar to FIG. 1A using another approach to flex the left ribs of the patient.

There is shown in FIG. 1 a patient 10 lying on an operating table 12 with a pillow 14 beneath his head and another pillow 16 beneath his right rib cage so as to flex and extend his left rib cage 18 to increase the spacing between neighboring ribs. The same effect can be achieved using an articulated table 20, FIG. 1B, in place of table 12 and pillow 16 in FIG. 1A.

Figures 2, 3:
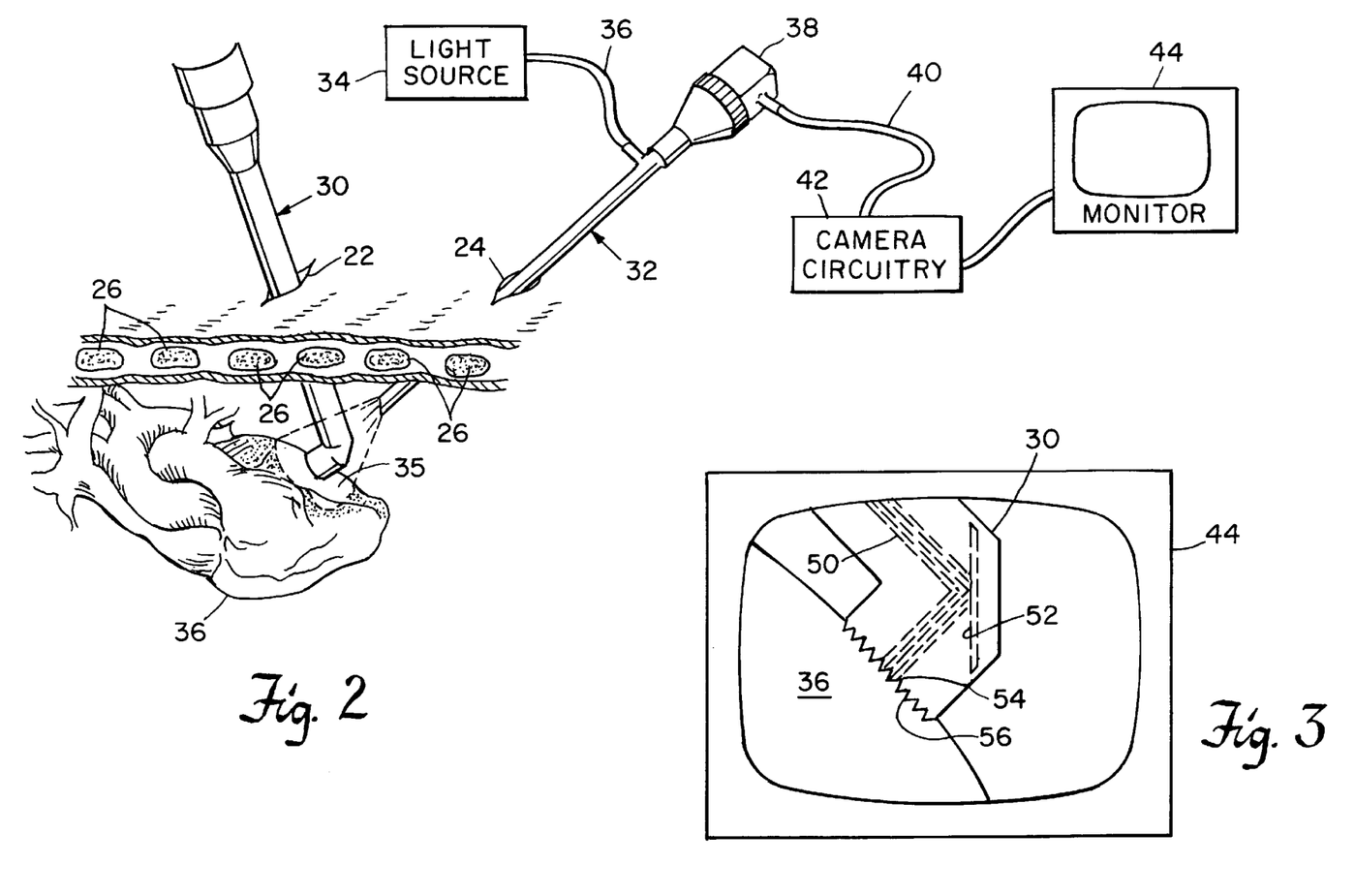
FIG. 2 is a cross-sectional schematic view showing the positioning of the thoracoscopic TMR handpiece and thoracoscope including the video display system attached to the thoracoscope.
FIG. 3 is an enlarged view of the monitor shown in FIG. 2 depicting the engagement of the handpiece with the heart wall.

With the ribs separated by the positioning shown in FIGS. 1A and 1B, two or more incision ports 22, 24, FIG. 2, are made between pairs of ribs 26. These incision ports are typically no more than two inches long at most. Into incision port 22 there is inserted thoracoscopic TMR handpiece assembly 30. Into incision port 24 is inserted thoracoscope 32. Light source 34 provides light through fiber optic bundle 36 and thoracoscope 32 to illuminate the area 35 of heart 36 contacted by handpiece assembly 30. The image of that scene in area 35 is transmitted by thoracoscope 32 to camera 38 interconnected through cable 40 with camera circuit 42 that provides an image to display monitor 44. Thoracoscopic TMR handpiece assembly 30 may be connected to an energy source for burning or ablating away the tissue to create a channel through the heart wall. Alternatively, handpiece assembly 30 may use mechanical or other means to cut the channel.

The actual image appearing on monitor 44 is depicted in FIG. 3, where handpiece assembly 30 can be seen transmitting laser beam 50 which is redirected off reflective surface 52 and out hole 54 in the roughened surface 56 of handpiece assembly 30. The roughened surface 56 helps keep handpiece assembly 30 in place on the slippery surface of heart 36. Typically, when using a laser powered system for creating the channels in the heart the surgeon will use a footswitch or other switch to actuate the laser. The laser is connected to an EKG which monitors the heartbeat of the patient and permits the laser to fire only during a predetermined window of the heartbeat contraction and expansion cycle following the actuation by the surgeon of the footswitch.

Figure 4:
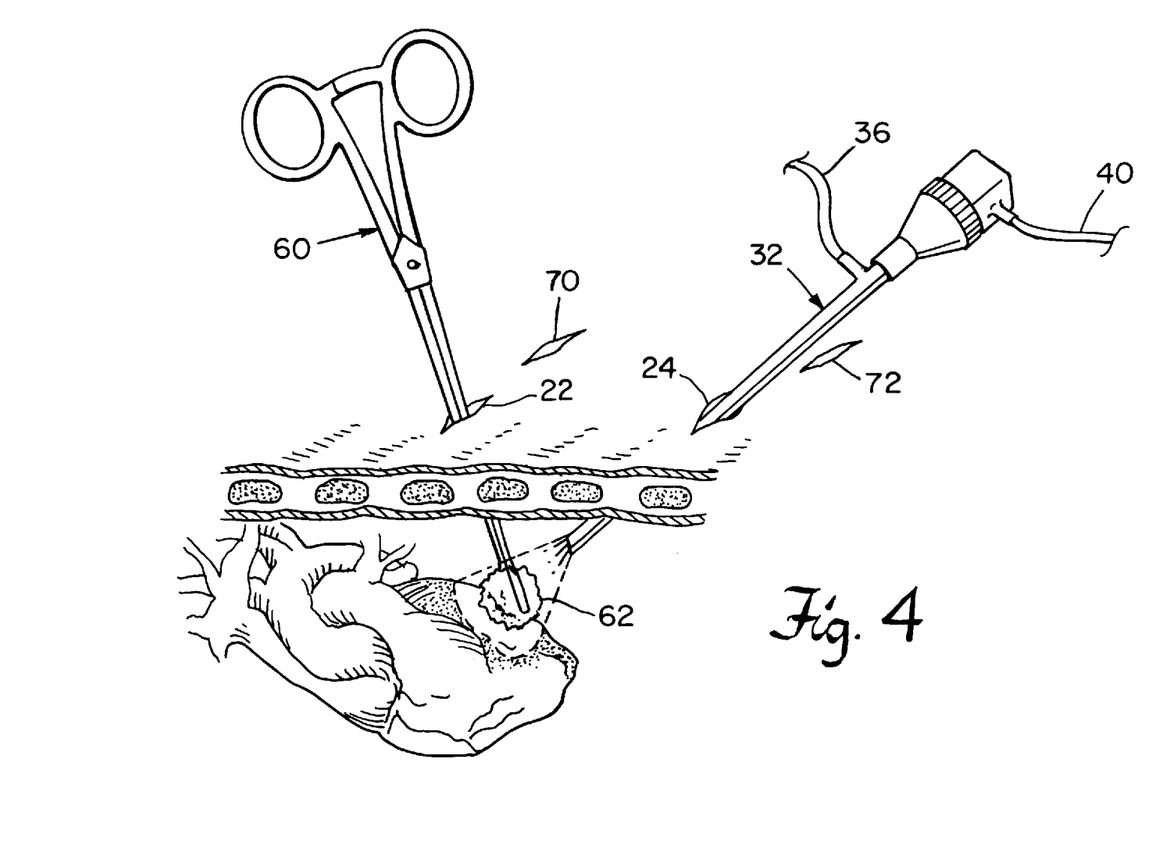
FIG. 4 is a schematic cross-sectional view similar to FIG. 2 with the thoracoscopic TMR handpiece replaced by a sponge-holding forceps.
Figure 5:
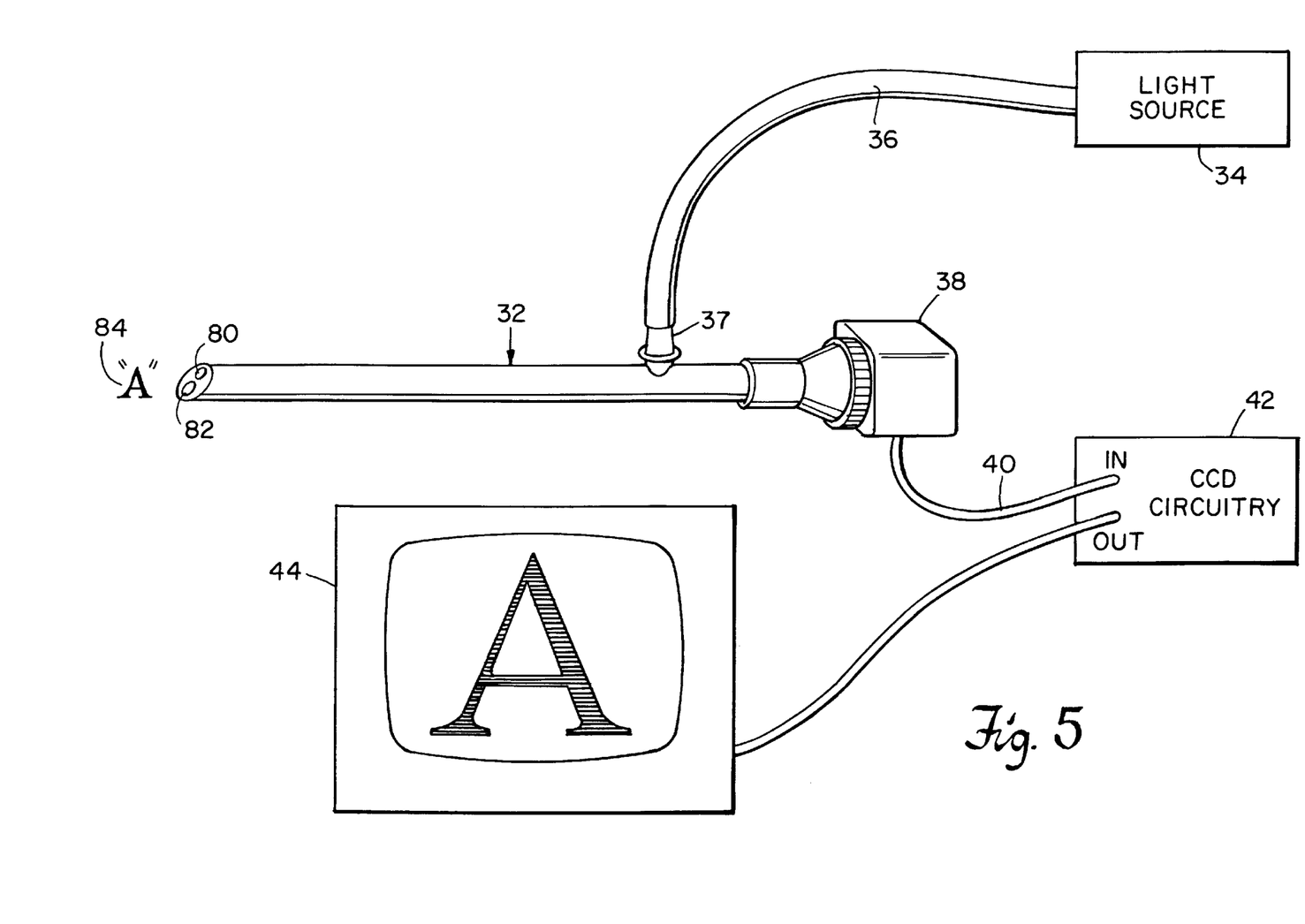
FIG. 5 is a more detailed diagram of the video display system of FIG. 2.
Figure 6:
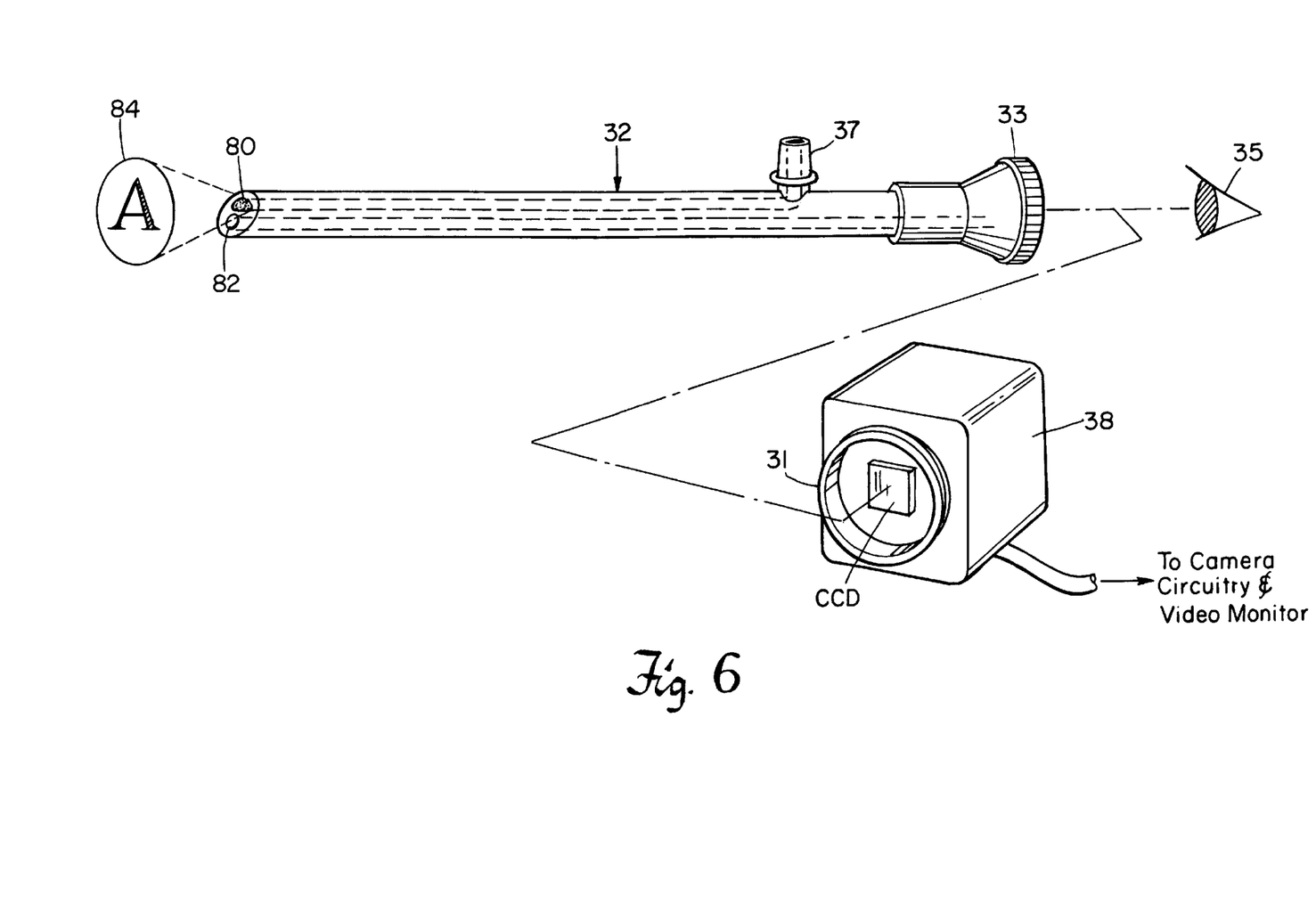
FIG. 6 is a more detailed view of the thoracoscope and camera of FIG. 3.

After the channel has been created the thoracoscopic TMR handpiece assembly 30 is removed and forceps 60, FIG. 4, bearing sponge 62 is inserted to cover the channel and stanch the blood flow until clotting occurs. Following this the procedure can be repeated one or many times. For example, in the next cycle of operation thoracoscope 32 will be placed in incision port 22 and thoracoscopic handpiece assembly 30 will be placed in incision port 24, and the entire action repeated. Following this, other incision ports 70, 72, . . . on can be used to accommodate either one and then the other of handpiece assembly 30, FIG. 2 and thoracoscope 32, FIG, 4 until all of the necessary channels have been created in the heart. Thoracoscope 32, FIG. 5, includes a fiber optic delivery system 80 which delivers the light from light source 34 through cable 36 attached at fitting 37 and an optical element 82 such as a lens for viewing the image shown as the letter A 84 and directing it to camera 38. Camera 38 may include an eyepiece connector 31 which can be easily disconnected from eyepiece 33, FIG. 6, so that the user may view with the naked eye 35.

Figures 7, 8A, 8B:
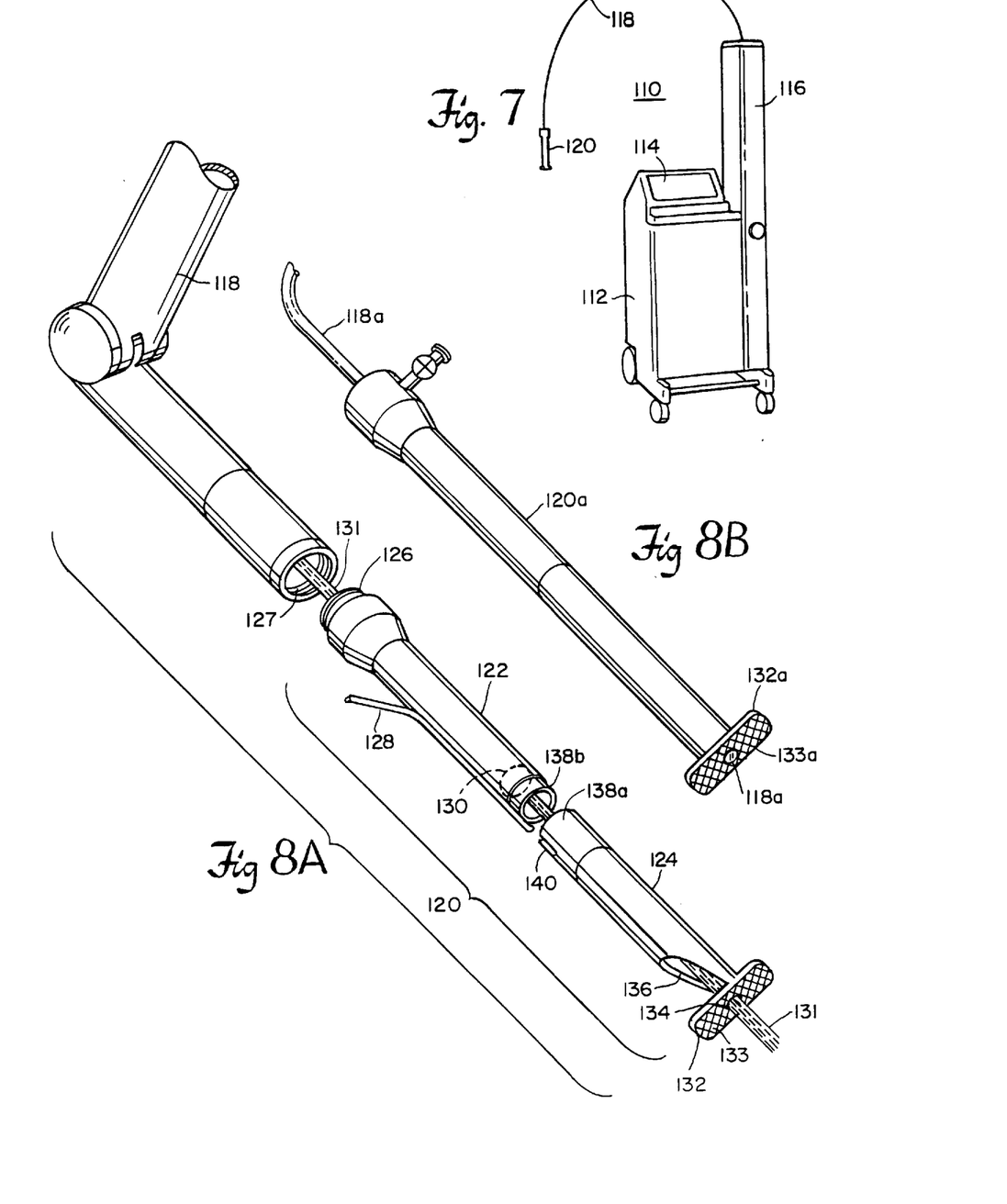
FIG. 7 is a three-dimensional view of a laser system which can be used in the method of this invention.
FIG. 8A is an enlarged, more detailed, exploded three-dimensional view of a portion of the articulated arm and handpiece of FIG. 7 in a first construction.
FIG. 8B is a view similar to FIG. 8A in which the arm and handpiece included a fiber optic feed and operating endoscope.

The handpiece assembly is explained in greater detail with respect to FIGS. 7–10. There is shown in FIG. 7 a surgical laser system 110 which includes a power supply and control 112 operated through control and monitor screen 114 to operate laser 116. The output from laser 116 is directed through articulated arm 118 to handpiece assembly 120 typically held by the operator or surgeon to direct the beam at the desired target.

Handpiece assembly 120, FIG. 8, includes barrel 122 and handpiece 124. Barrel 122 includes threaded portion 126 for connection to articulated arm 118 at threaded portion 127, and purge tube 128 for introducing a purge gas into handpiece 124. Handpiece 124 includes contacting wall 132 having a knurled surface 133 for preventing slippage of handpiece 124 on the heart during surgery. There is an aperture 134 in contacting wall 132 through which laser beam 131 exits to strike the heart. Lens 130, shown in phantom in barrel 122, focuses laser beam 131 at a predetermined distance, typically at or near aperture 134. Handpiece 124 also includes cutout portion 136 through which the user can view the beam as it enters aperture 134. Cutout portion 136 also acts as a venting hole for the ablative plume which rises from the heart or other tissue struck by the laser beam 131. Handpiece 124 includes coupling portion 138a which slides over coupling portion 138b of barrel 122 in order to effect a friction fit. There is a slot 140 in coupling portion 138a which accepts the distal end of purge tube 128.

Barrel 122 and handpiece 124 typically have diameters in the range of ⅜ inch to ⅝ inch. This allows the handpiece assembly to be slid between adjacent ribs of a patient in order to access the heart without opening the chest cavity. Generally, the space between ribs of a patient is approximately 0.5". As can be seen in the figure, contacting wall 132 of handpiece 124 is formed such that the width of the contacting wall is the same as the diameter of handpiece 124 while the length of contacting wall 132 is approximately twice the diameter of handpiece 124. This increases the area of contact with the heart and therefore decreases the pressure of force per unit area on the heart. It also provides a more stable platform by which to maintain perpendicularity between the beam 131 and the heart wall and reduces the chances of the handpiece puncturing or otherwise damaging the heart tissue. However, the narrow width of contacting wall 132 allows handpiece assembly 120 to be slid between adjacent ribs of the patient.

Purge tube 128 is connected to a purge gas source which provides a gas such as carbon dioxide under a gentle flow, typically one to three liters per minute, to create a back pressure from lens 130 forward into handpiece 124. This keeps any debris from the ablation from contacting and obscuring or damaging lens 130.

Although handpiece assembly 120 has been shown with handpiece 124 as a straight member, this is not necessary: handpiece 124 may be constructed at any desired angle. For example, handpiece 124a, FIG. 9, may include a right angle configuration so that contacting wall 132a and aperture 134a are facing at a right angle to the path of laser beam 131. A reflective surface 142 is provided to reflect the beam from an incoming path parallel to axis 144 to the outgoing path parallel to axis 146. One or more vent holes 148 may be provided for exhausting gas and ablated tissue aided by the back pressure caused by the introduction of the purge gas through purge tube 128. In this embodiment, reflective surface 142 is enclosed as much as possible in order to minimize contamination from body fluids prior to firing the laser.

In the preferred constructions, barrel 122 is formed of stainless steel due to its strength, its ability to be sterilized repeatedly and its ability to withstand heat from the unfocused laser before it is focused by lens 130. Purge tube 128 is also formed of stainless steel and is typically welded to barrel 122. Handpiece 124a is typically injection molded of medical grade clear acrylic. This allows the surgeon to monitor the laser beam as it passes through the handpiece, allows more effective cleaning of the inside of the handpiece during surgery and enhances the disposability of the handpiece. Coupling portion 138a of handpiece 124a, however, is formed of the same stainless steel as barrel 122. This allows for a tighter friction fit between handpiece 124 and barrel 122 which is not affected by changes in temperature due to the heat of the laser. Threaded portion 126 of barrel 122 is typically formed of an electrical insulating material such as Delrin to electrically insulate the patient from the laser system, and to avoid additional grounding locations for electrocautery devices used on the patient. Also, lens 130 has a five-inch focal length which focuses beam 131 at aperture 134 in the case of the embodiment of FIG. 8 and at aperture 134a in the case of the construction of FIG. 9.

Figure 9:
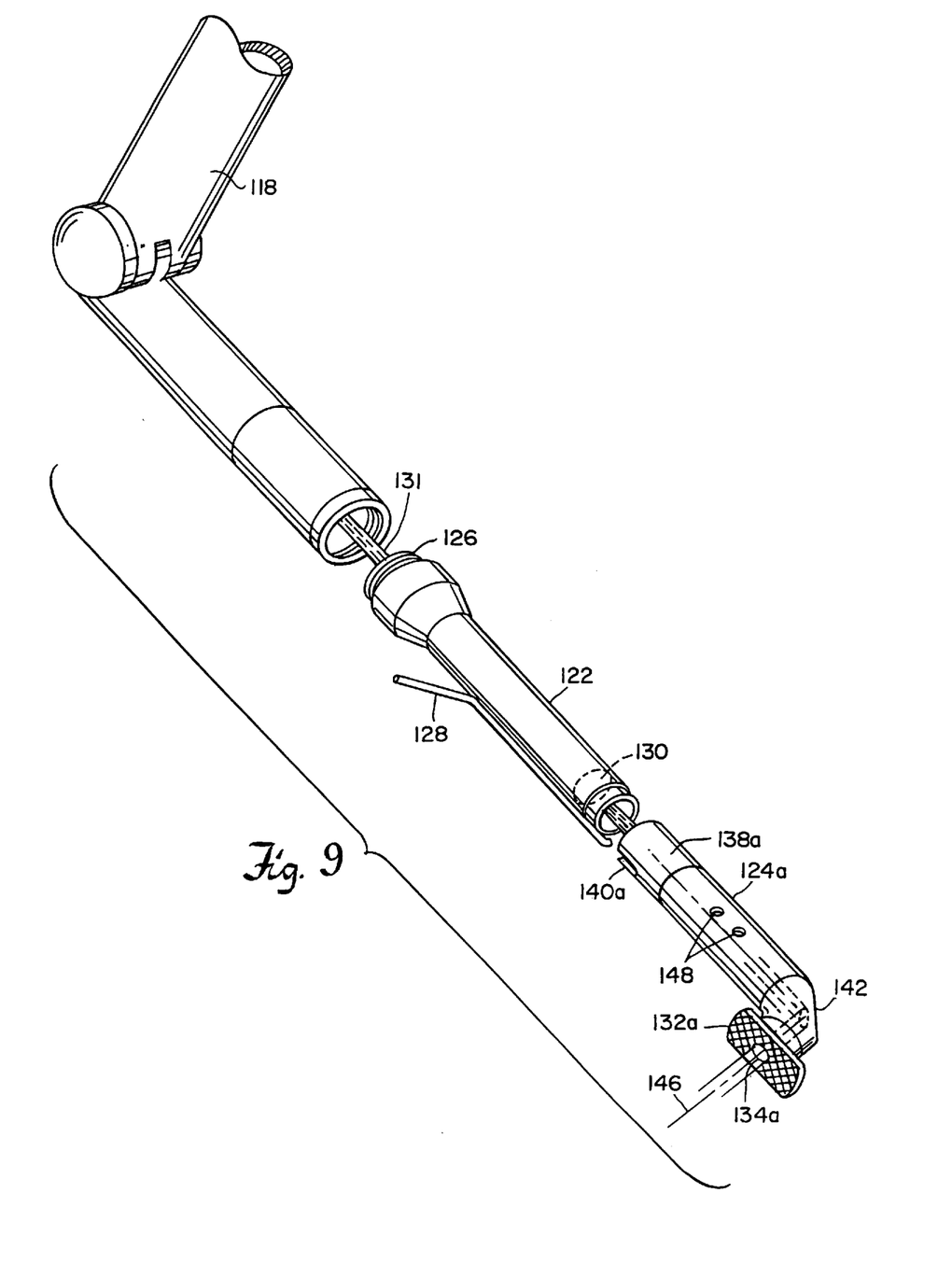
FIG. 9 is an enlarged, more detailed, exploded three-dimensional view of a portion of the articulated arm and handpiece of FIG. 7 in a second construction.
Figure 10:
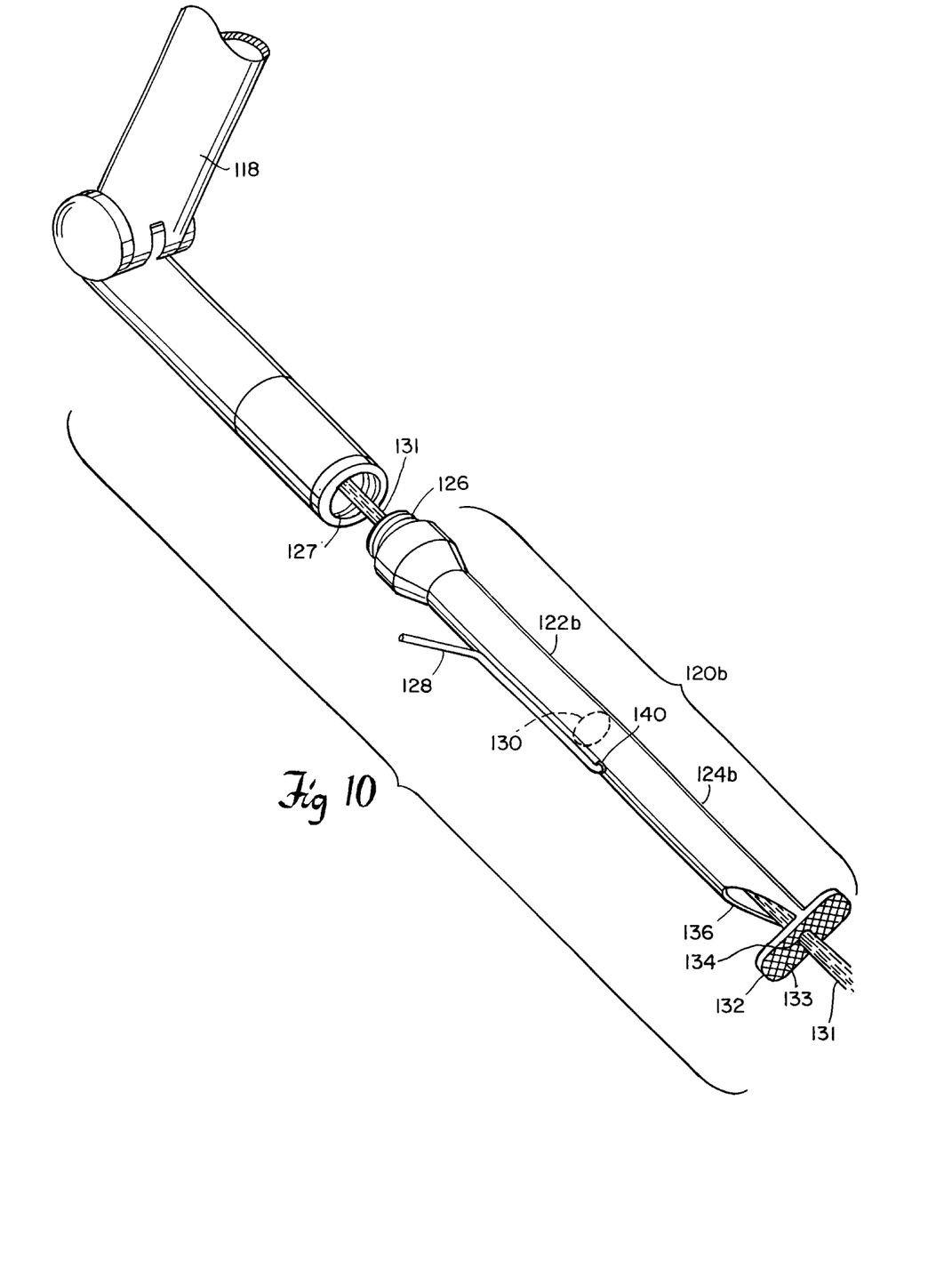
FIG. 10 is an enlarged, more detailed exploded three-dimensional view of a portion of the articulated arm in FIG. 7 and another construction in which the barrel and handpiece are integral.

While handpiece assembly 120, FIGS. 8 and 9, has been shown as including two separate sections, barrel 122 and handpiece 124 (124a), that is not necessary. Handpiece assembly 120b, FIG. 10, may be made as a single integral unit including both barrel 122b and handpiece 124b. Alternatively, the arm 118 and handpiece assembly 120 can include a fiber optic or flexible waveguide 118a and operating endoscope 120a, as shown in phantom in FIG. 7 and in more detail in FIG. 8B.

The timed firing is explained in greater detail with respect to FIGS. 11–15B.

Figure 11:
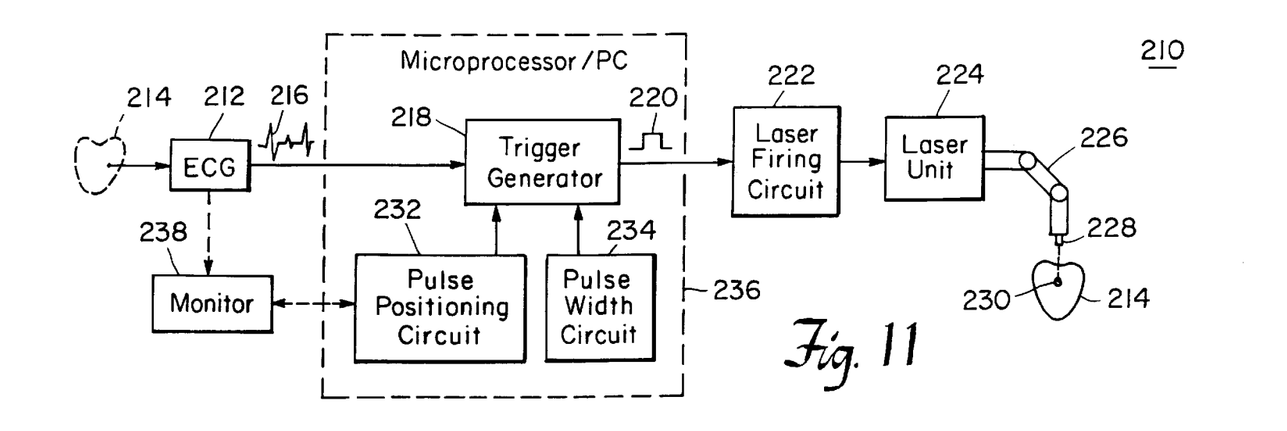
FIG. 11 is a schematic block diagram of a heart-synchronized pulsed laser system.

There is shown in FIG. 11 a heart-synchronized pulsed laser system 210 with electrocardiogram unit 212 connected to a heart 214 which is to undergo the surgery. The ECG signal 216 is delivered to trigger generator 218, which provides a trigger pulse 220 to laser firing circuit 222, which in turn energizes laser unit 224 including a laser power supply and a laser to produce a pulsed laser beam through articulated optical arm 226 into optical handpiece 228 to make a hole 230 in heart 214. The position of trigger pulse 220 in the heartbeat cycle of ECG signal 216 is determined by pulse positioning circuit 232. The width of the pulse 220 and its duration during the heartbeat cycle is determined by pulse width circuit 234. Trigger generator 218 as well as pulse positioning circuit 232 and pulse width circuit 234, may be included as an additional board in a PC or a microprocessor 236, in which case the system can be controlled through the computer keyboard and suitable software. PC 236 and ECG 212 may have separate monitors, or they may have a single monitor 238 which displays both the ECG and information about the trigger pulse 220. Trigger generator 218 may include a marker pulse circuit 250 which provides marker pulse 252 and trigger pulse circuit 254 which responds to marker pulse 252 to create trigger pulse 220. Alternatively, marker pulse circuit 250 is included in the ECG itself in some cases.

Figure 12:
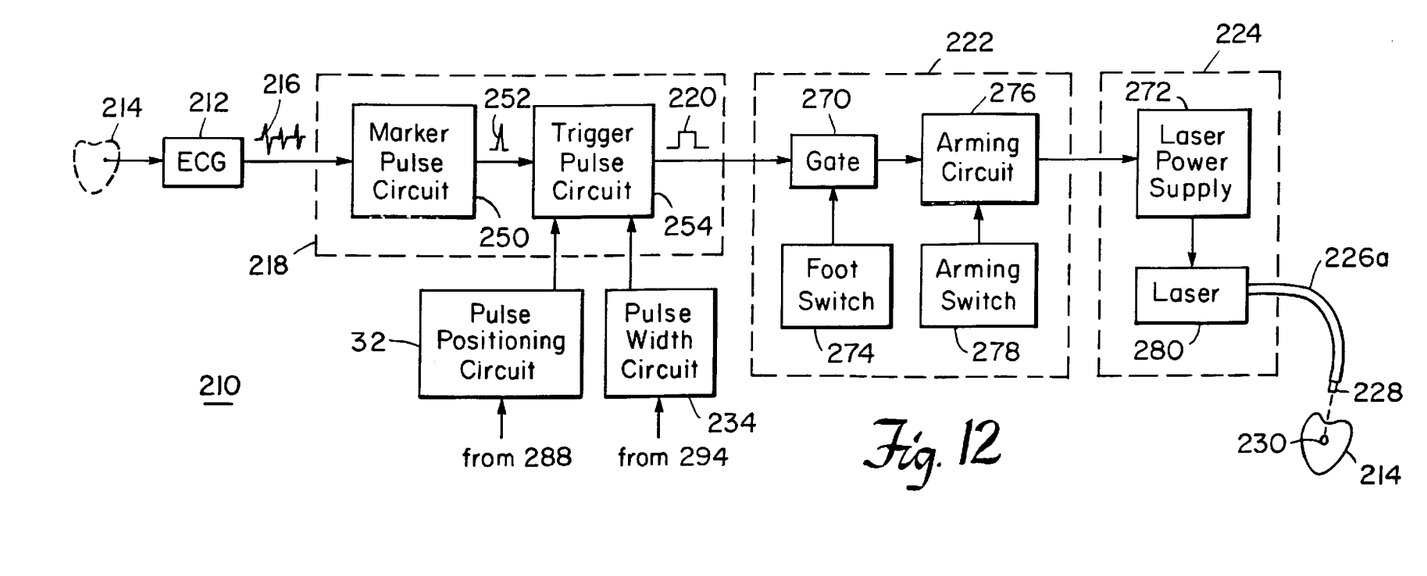
FIG. 12 is a more detailed diagram of the system of FIG. 11.
Figure 13:
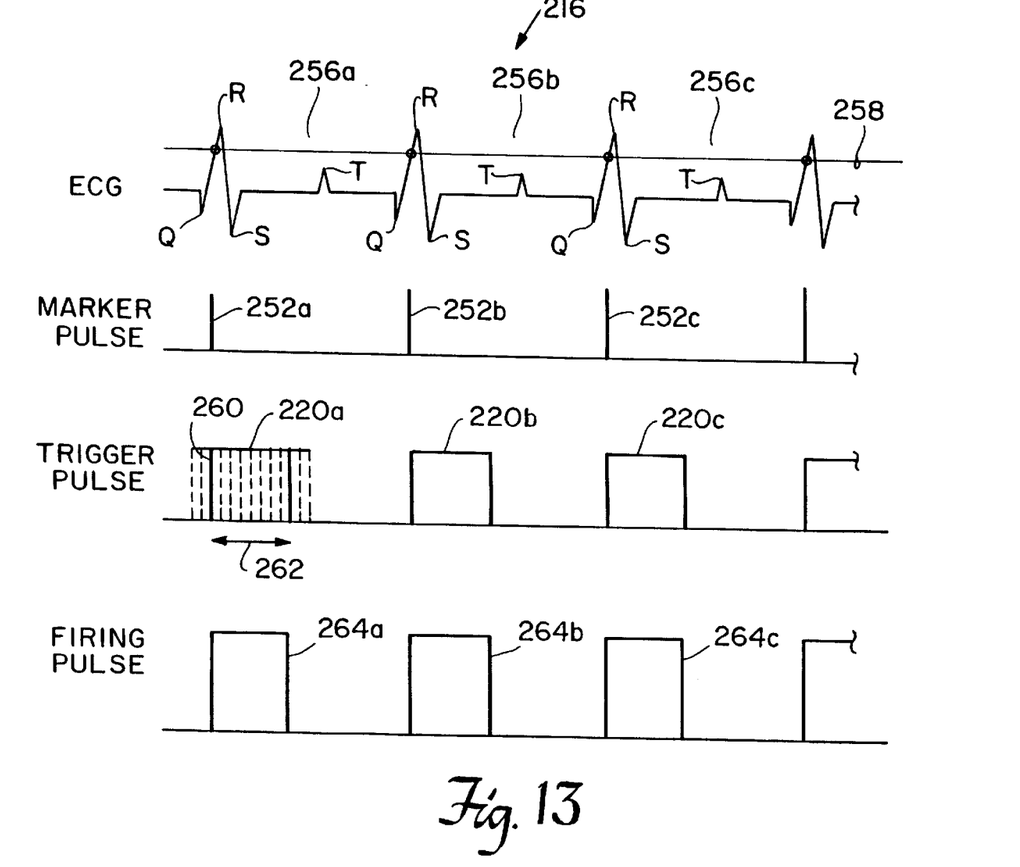
FIG. 13 illustrates the ECG signal, marker pulse, trigger pulse and firing pulse waveforms occurring in the heart-synchronized pulsed laser system described in FIGS. 11 and 12.

This can be better understood with reference to FIG. 13, where ECG signal 216 may be seen as consisting of a series of heartbeat cycles 256a, 256b, 256c, each of which contains the waveforms Q, R, S and T. Where waveform R crosses preselected threshold 258, marker pulses 252a, 252b, 252c are created. Trigger pulses 220a, 220b, 220c are then created by trigger pulse circuit 254. The position of the leading edge 260 and the overall width 262 of each trigger pulse 220 is determined, respectively, by pulse positioning circuit 232 and pulse width circuit 234. In response to trigger pulse 220, a firing pulse 264 indicated as 264a, 264b and 264c, FIG. 13, is created to energize laser unit 224, FIGS. 11 and 12.

In FIG. 12, laser firing circuit 222 is shown to include gate 270 which generally inhibits the delivery of trigger pulse 220 to laser power supply 272 in laser unit 224. The inhibiting effect of gate 270 can be overcome when the surgeon steps on foot switch 274. Trigger pulse 220 is still inhibited, however, by arming circuit 276 which in turn can have its inhibiting effect overcome by the operation of arming switch 278. This double lock on the delivery of trigger pulse 220 to laser power supply 272 ensures that the firing of the laser is truly desired and not accidental. Thus the surgeon must first arm the system by operating arming switch 278 to enable arming circuit 276. Then and only then is he able to pass the next occurring trigger pulse 220 through gate 270 to the laser power supply 272 by actuating his foot switch 274. Also included in laser unit 224 is a standard $CO_2$ laser 280. The output of laser 280 may be delivered though a fiber optic element 226a to handpiece 228.

Figure 14:
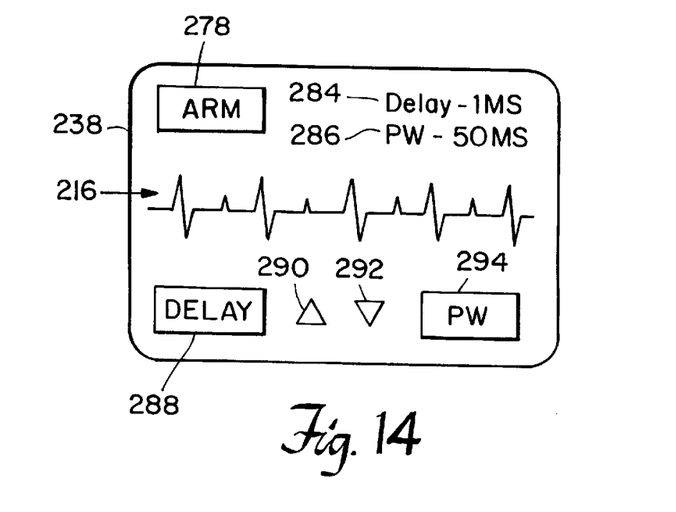
FIG. 14 is an illustration of a touch-sensitive monitor that may be used in conjunction with the system of FIGS. 11 and 12.

Monitor 238, FIG. 14, may display both the ECG signal 216 and the display of the delay 284 has been introduced by pulse positioning circuit 232, FIG. 12, which delay is indicated as one millisecond in FIG. 14. It may also include the pulse width 286 shown as 50 milliseconds selected by the pulse width circuit 234, FIG. 12. Monitor 238 may also include a delay selection switch 288 which when pressed enables one to increase or decrease the delay time by simply touching the up 290 or down 292 arrows on the screen. Pulse width touch switch 294 may be used in the same fashion to adjust the pulse width duration.

Figure 15A:
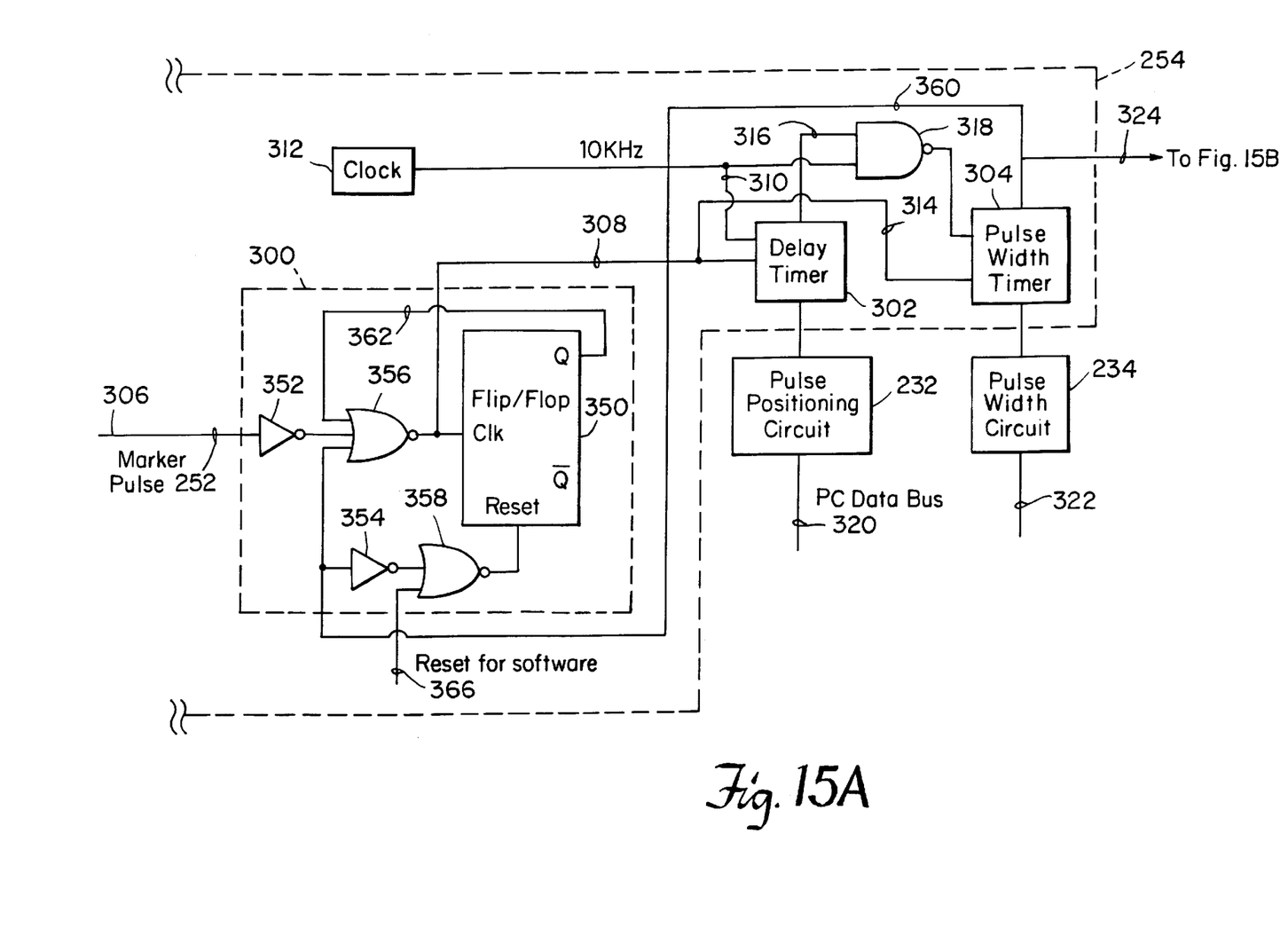
FIG. 15A is a more detailed schematic diagram of the trigger pulse circuit, pulse positioning circuit and pulse width circuit of FIG. 12.

Trigger pulse width circuit 254, FIG. 15A, may include an anti-false trigger pulse circuit 300 which prevents a false firing or second firing of the system when a firing sequence is already in progress. Also included in trigger pulse circuit 254 is a delay timer 302 and a pulse width timer 304. When marker pulse 252 on line 306 is permitted to pass through anti-false trigger pulse circuit 300, the marker pulse is input on line 308 to delay timer 302. The conjunction of the marker pulse with the input on line 310 from 10 KHz clock 312 causes delay timer 302 to set the position of the leading edge of the trigger pulse. The appearance of the marker pulse on line 308 also is delivered as an enable signal on line 314 to preset pulse width timer 304. When the leading edge position of the trigger pulse has been set by delay timer 302 a signal is provided on line 316 to NAND gate 318, which in conjunction with a signal from clock 312 causes the trigger impulse to be expanded to a predetermined width in pulse with timer 304. The specific positioning of the leading edge of the trigger pulse by delay timer 302 is controlled by pulse positioning circuit 232 which is typically a time delay data latch under control of the computer via the data bus 320. Similarly, the duration of the pulse imparted by pulse width timer 304 is controlled by pulse width circuit 234, typically a pulse width time data latch under control of the microprocessor or PC via bus 322. The trigger pulse then is delivered over line 324 to gate 270 which may include simply an NAND gate 326.

Figure 15B:
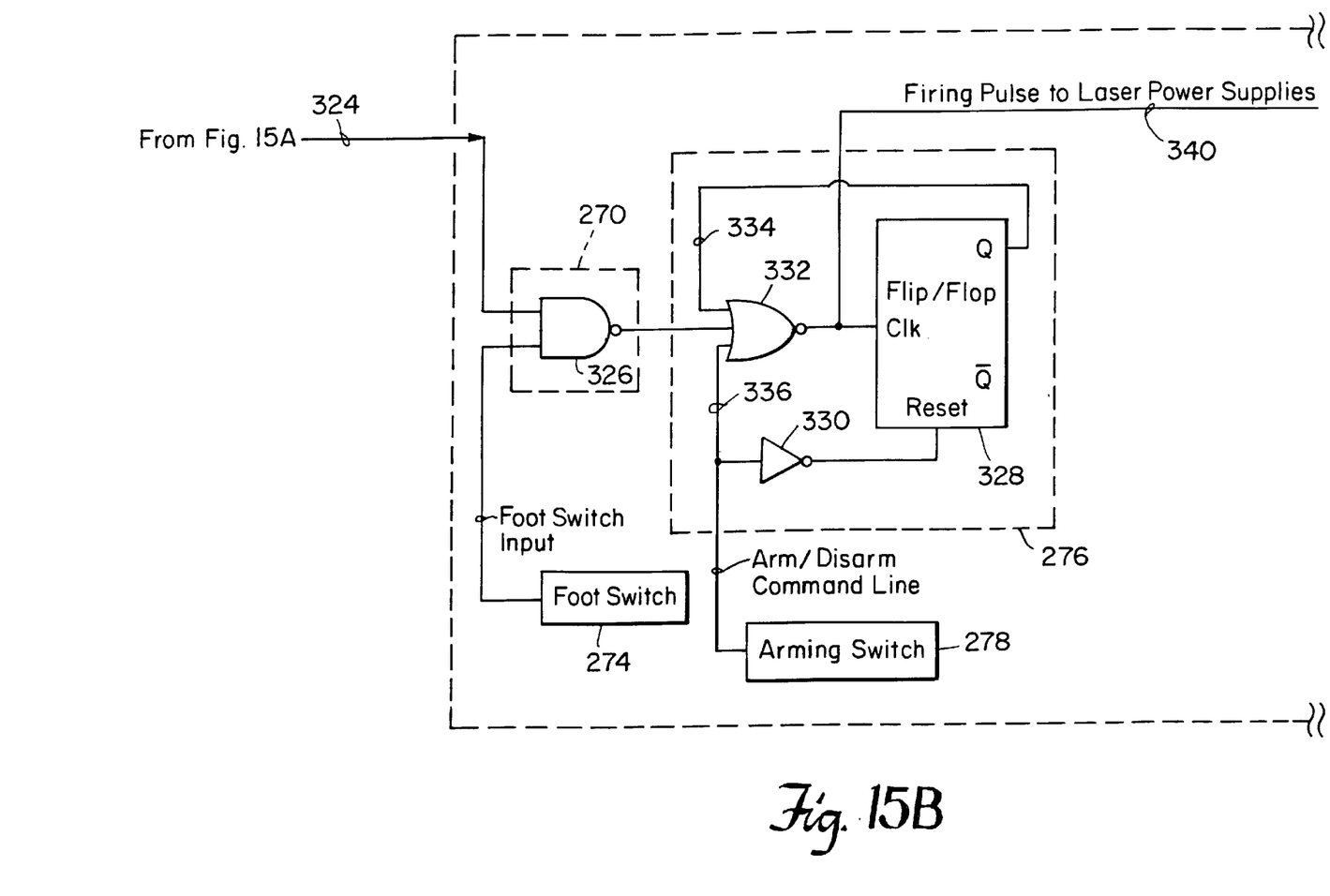
FIG. 15B is more detailed schematic diagram of the laser firing circuit of FIG. 12.

Arming circuit 276, FIG. 15B, includes flip-flop 328, inverter 330, and NOR gate 332. When arming switch 278 is actuated, the signal to inverter 330 resets flip-flop 328 so that now there is a proper output on line 334 from flip-flop 328 into NOR gate 332 as well as the proper input from arming switch 278 on line 336 into NOR gate 332. Thus, when next the trigger pulse arrives on line 324, if the doctor operates the foot switch 274 the pulse will be passed through NAND gate 326 and NOR gate 332 to pass the trigger pulse on line 340 to laser power supply 272. When the trigger pulse passing through NOR gate 332 ends, the clock input to flip-flop 328 is no longer enabled and the output on line 334 ceases so that NOR gate 332 is no longer enabled to pass subsequent trigger pulses to line 340 and laser power supply 272.

The anti-false trigger pulse circuit 300, FIG. 15A, uses a flip-flop 350, two inverters 352 and 354, and two NOR gates 356 and 358. When a trigger pulse is supplied on line 324 by pulse width timer 304, it is also simultaneously placed on line 360 which is connected to inverter 354 and to NOR gate 356. At the end of the trigger pulse, the proper level appears on line 360 to enable NOR gate 356 and to reset flip-flop 350 through inverter 354 and NOR gate 358. When flip-flop 350 is reset it provides a second enabling input on line 362 to NOR gate 356. Thus when next a marker pulse 252 is delivered on line 306 and passed by inverter 352 to NOR gate 356, it is passed to line 308 and thus on to delay timer 302. The marker pulse 252 appearing on line 308 also clocks flip-flop 350 so that the proper signal is no longer on line 362 and NOR gate 356 is disabled. Until a reset occurs from the software on line 366 or the end of the trigger pulse level occurs on line 360 no further marker pulses will be passed.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A video assisted thoracoscopic transmyocardial revascularization surgical method comprising:

making at least two spaced incision ports between the ribs of a patient proximate the patient's heart;

inserting through one of said ports means for creating a channel through the heart wall;

inserting through the other incision port a thoracoscope connected to a video display system;

viewing the heart of the patient through said video display system and positioning said means relative to the heart; and actuating said means to create a channel through the wall of the patient's heart including the step of sensing the contraction and expansion of the heart and actuating said means only at a predetermined time in the expansion and contraction of the beating heart.

2. The method of claim 1 in which the means for creating and thoracoscope positions are interchanged and the actuation of the means for creating is repeated.

3. The method of claim 1 in which the video display system includes a light source, a video camera and a monitor.

4. The method of claim 1 in which the means for creating includes an elongate barrel having a narrow width sized to fit between the ribs of a patient; an elongate handpiece extending from said barrel and having a similarly narrow width commensurate with said barrel; and a contacting surface on the distal end of said handpiece for contacting the wall of the patient's heart; said contacting surface having a width in a first dimension which is approximately that of said handpiece for fitting between the ribs of a patient and having a width in a second dimension which is larger to effect an area of said contacting surface which is substantially larger than the cross-sectional area of said handpiece.

5. The method of claim 1 further including withdrawing said means for creating from its incision port and inserting through that incision port forceps with a sponge to cover the channel created through the heart wall and stanch blood flow.

6. The method of claim 1 further including positioning the patient on his right side in the lateral decubitus position with the left rib cage exposed.

7. The method of claim 1 in which said means for creating includes an operating endoscope and a fiberoptic feed.

* * * * *